United States Patent [19]

Stoltefuss et al.

[11] Patent Number: 5,015,650

[45] Date of Patent: May 14, 1991

[54] CIRCULATION-ACTIVE BASIC 4-ARYL-DHP AMIDES

[75] Inventors: Jürgen Stoltefuss, Haan; Eckhard Schwenner, Wuppertal; Rainer Gross, Wuppertal; Siegbert Hebisch, Wuppertal; Matthias Schramm, Cologne; Martin Bechem, Wuppertal; Claudia Hirth, Wuppertal; Johannes-Peter Stasch, Wuppertal, all of Fed. Rep. of Germany

[73] Assignee: Bayer Aktiengesellschaft, Leverkusen, Fed. Rep. of Germany

[21] Appl. No.: 413,365

[22] Filed: Sep. 27, 1989

[30] Foreign Application Priority Data

Oct. 5, 1988 [DE] Fed. Rep. of Germany ....... 3833892

[51] Int. Cl.$^5$ .................. A61K 31/455; C07D 211/86
[52] U.S. Cl. ...................................... 514/356; 546/316
[58] Field of Search ................ 546/321, 316; 514/356, 514/355

[56] References Cited

U.S. PATENT DOCUMENTS 4,492,703 1/1985 Goldmann et al. ................. 546/139
4,772,612 9/1988 Goldmann et al. ................. 546/263
4,874,773 10/1989 Hisaki et al. ........................ 514/355

FOREIGN PATENT DOCUMENTS 2228377 1/1974 Fed. Rep. of Germany .

OTHER PUBLICATIONS

Takenaka et al., CA 108: 160946q.
Kauco et al., CA 85: 78008h.

*Primary Examiner*—Jane T. Fan
*Attorney, Agent, or Firm*—Sprung Horn Kramer & Woods

[57] ABSTRACT

Circulation active dihydropyridine amides of the formula

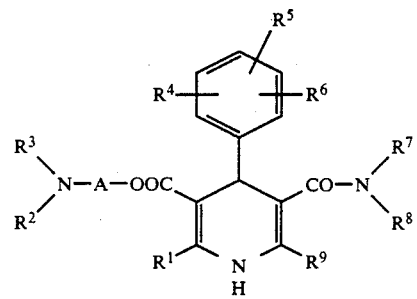

in which
$R^6$ represents a group of the formula $-O-(CH_2)_n-R^{10}$, $-S-(CH_2)_n-R^{10}$, $-O-SO_2-(CH_2)_nR^{10}$ or $-O-CO-(CH_2)_n-R^{10}$
in which
n denotes 0 to 4,
and
$R^{10}$ denotes cyclohexyl, aryl or a heterocyclic ring, and physiologically acceptable salts thereof.

10 Claims, No Drawings

CIRCULATION-ACTIVE BASIC 4-ARYL-DHP AMIDES

The present invention relates to dihydropyridine amides, processes for their preparation and their use in medicaments, in particular as circulation-influencing medicaments.

It is known that diethyl 1,4-dihydro-2,6-dimethyl-4-phenyl-pyridine-3,5-dicarboxylate is obtained when ethyl benzylideneacetoacetate is reacted with ethyl β-aminocrotonate or ethyl acetoacetate and ammonia [E. Knoevenagel, Ber. Dtsch. Chem. Ges. 31, 743 (1898)].

It is furthermore known that certain 1,4-dihydropyridines have interesting pharmacological properties [F. Bossert, W. Vater, Naturwissenschaften 58, 578 (1971)]. In EP-A 220,653, it has been disclosed that 3-aminocarbonyl-1,4-dihydropyridine-5-carboxylic acid derivatives are obtained when alkyl o-(or m-)nitrobenzylideneacetoacetates are reacted with 3-aminocrotonamides in a cyclization reaction.

The present invention relates to new dihydropyridine amides of the general formula (I)

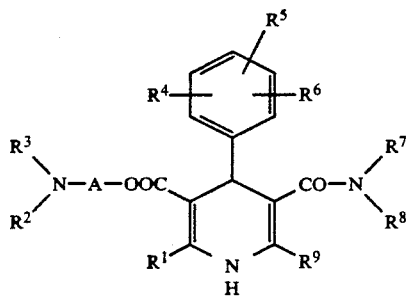

in which
$R^1$ and $R^9$ are identical or different and
represent straight-chain, branched or cyclicalkyl having up to 6 carbon atoms, which is optionally substituted by hydroxyl, cyano, phenyl or halogen, or represent cyano or phenyl, $R^2$ and $R^3$ are identical or different and represent hydrogen, straight-chain or branched alkyl, alkenyl or alkynyl in each case having up to 12 carbon atoms, which may be substituted by halogen, hydroxyl, alkoxy having up to 8 carbon atoms, cyano, trifluoromethyl, alkylthio having up to 8 carbon atoms, alkylcarbonyl having up to 8 carbon atoms in the alkyl radical, carboxyl or alkoxycarbonyl having up to 8 carbon atoms, or by phenyl which is optionally substituted by nitro, phenyl, cyano, trifluoromethyl, trifluoromethoxy, alkyl having up to 4 carbon atoms, halogen or alkoxy having up to 4 carbon atoms, or represent cycloalkyl having 3 to 8 carbon atoms or
represent aryl having 6 to 12 carbon atoms, which may optionally be monosubstituted to trisubstituted by identical or different substituents from the series comprising nitro, cyano, halogen, alkyl having up to 6 carbon atoms, alkoxy having up to 6 carbon atoms, alkylthio having up to 6 carbon atoms, carbamoyl, dialkylcarbamoyl in each case having up to 6 carbon atoms per alkyl group, trifluoromethyl, trifluoromethoxy, difluoromethoxy, trifluoromethylthio, amino, alkylamino having up to 8 carbon atoms, dialkylamino in each case having up to 8 carbon atoms per alkyl group, acetylamino or benzoylamino, or $R^2$ and $R^3$ together form a 5- to 7-membered saturated or unsaturated heterocyclic ring which may contain an oxygen atom, a sulphur atom or an additional nitrogen atom as a heteroatom, which may optionally be substituted by a group $R^{13}$ which represents hydrogen, a straight-chain or branched, saturated or unsaturated alkyl group having up to 10 carbon atoms, which may optionally be substituted by phenyl which may be substituted by halogen, alkyl having up to 4 C atoms, alkoxy having up to 4 C atoms, nitro and haloalkyl having up to 2 C atoms or represents phenyl which may optionally be substituted by halogen, cyano, nitro, alkyl having up to 2 C atoms, alkoxy having up to 2 C atoms or haloalkyl having up to 2 C atoms, $R^4$ and $R^5$ are identical or different and
represent hydrogen, halogen, alkyl having up to 6 carbon atoms, alkoxy having up to 6 carbon atoms, alkylthio having up to 4 carbon atoms, cyano, nitro, dialkylamino in each case having up to 4 carbon atoms per alkyl group, trifluoromethyl, trifluoromethoxy, difluoromethoxy or trifluoromethylthio, $R^6$ represents a group of the formula $-O-(CH_2)_n-R^{10}$, $-S-(CH_2)_n-R^{10}$, $-O-SO_2-(CH_2)_nR^{10}$ or $-O-CO-(CH_2)_n-R^{10}$
in which
n denotes 0 to 4,
and
$R^{10}$
denotes cyclohexyl or aryl having 6 to 10 carbon atoms, which can be monosubstituted to tetrasubstituted by identical or different substituents from the series comprising halogen, cyano, nitro, trifluoromethyl, trifluoromethoxy, difluoromethoxy, trifluoromethylthio, alkyl having up to 6 carbon atoms, alkoxy having up to 6 carbon atoms, alkylthio having up to 4 carbon atoms, amino, alkylamino having up to 6 carbon atoms, dialkylamino in each case having up to 6 carbon atoms per alkyl group or acetylamino or
denotes a 5- to 7-membered saturated or unsaturated heterocyclic ring which may contain an oxygen atom, a sulphur atom or two nitrogen atoms as heteroatoms,
and
$R^7$ and $R^8$ are identical or different and in each case
represent hydrogen,
represent cycloalkyl having 3 to 8 carbon atoms or
represent straight-chain or branched alkyl or alkenyl in each case having up to 18 carbon atoms, which are optionally substituted by halogen, hydroxyl, alkoxy having up to 8 carbon atoms, alkylthio having up to 8 carbon atoms, alkylcarbonyl having up to 8 carbon atoms in the alkyl radical, carboxyl or alkoxycarbonyl having up to 8 carbon atoms, cyano or by phenyl or phenoxy groups which are optionally substituted by nitro, cyano, trifluoromethyl, trifluoromethoxy, alkyl having up to 4 carbon atoms or alkoxy having up to 4 carbon atoms, or where the radicals cycloalkyl, alkyl or alkenyl are optionally substituted by a group of the formula $-NR^{11}R^{12}$,
in which
$R^{11}$ and $R^{12}$ are identical or different, and in each case denote hydrogen, alkyl having up to 8 carbon atoms, aralkyl having 7 to 14 carbon atoms, aryl having 6 to 10 carbon atoms, acetyl, benzoyl, alkylsulphonyl having up to 6 carbon atoms or phenylsulphonyl, or $R^7$ and $R^8$ in each case represent aryl having 6 to 10 carbon atoms, which is monosubstituted to trisubstituted by identical or different substituents from the series comprising nitro, cyano, halogen, alkyl having up to 6 carbon atoms, alkoxy having up to 6 carbon atoms, alkylthio having up to 6 carbon atoms, trifluoromethyl, trifluoromethoxy, difluoromethoxy, trifluoromethylthio, amino, alkylamino having up to 4 carbon atoms, dialkylamino having up to 4 carbon atoms per alkyl group, acetylamino or benzoylamino, or represent a 5- to 7-membered saturated or unsaturated heterocyclic ring which may contain an oxygen atom, a sulphur atom or an NH or N-alkyl group (1-4 C atoms) as an additional heteroatom, and A represents a straight-chain, branched or cyclic, saturated or unsaturated hydrocarbon radical having up to 12 carbon atoms, which may optionally be interrupted by an oxygen or sulphur atom or an $N-R^{14}$ group, in which $R^{14}$ may denote hydrogen, alkyl having up to 4 carbon atoms, benzyl or phenethyl, and/or which may be substituted by halogen, hydroxyl, acetoxy, carboxyl, alkoxycarbonyl having up to 8 carbon atoms or phenyl which may optionally be substituted by halogen, alkyl having up to 2 carbon atoms, alkoxy having up to 2 carbon atoms, halomethyl, halomethoxy, hydroxyl or cyano, and their physiologically acceptable salts, in the form of their diastereomer mixtures, racemates and antipodes.

The compounds according to the invention exist in stereoisomeric forms which either behave as image and mirror image (enantiomers) or which do not behave as image and mirror image (diastereomers). The invention relates both to the antipodes and to the racemates as well as the diastereomer mixtures. The racemates, just like the diastereomers, can be resolved into the stereoisomerically uniform components in a known manner (cf. E. L. Eliel, Stereochemistry of Carbon Compounds, McGraw Hill, 1962).

Physiologically acceptable salts may be salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

Preferred compounds of the general formula (I) are those in which $R^1$ and $R^9$ are identical or different and in each case represent straight-chain or branched alkyl having up to 4 carbon atoms, which is optionally substituted by hydroxyl or phenyl, $R^2$ and $R^3$ are identical or different and represent hydrogen, straight-chain or branched alkyl, alkenyl or alkynyl each having up to 8 carbon atoms, which may be substituted by halogen, hydroxyl, alkoxy having up to 4 carbon atoms, cyano, trifluoromethyl, alkylthio having up to 4 carbon atoms, alkylcarbonyl having up to 4 carbon atoms in the alkyl radical, carboxyl or alkoxycarbonyl having up to 8 carbon atoms, or by phenyl which is optionally substituted by nitro, phenyl, trifluoromethyl, trifluoromethoxy, alkyl having up to 2 carbon atoms, halogen or alkoxy having up to 2 carbon atoms, or represent cycloalkyl having 3 to 8 carbon atoms or represent aryl having 6 to 10 carbon atoms, which may be monosubstituted or disubstituted by identical or different substituents from the series comprising nitro, cyano, halogen, alkyl having up to 4 carbon atoms, alkoxy having up to 4 carbon atoms, alkylthio having up to 4 carbon atoms, trifluoromethyl, trifluoromethoxy, difluoromethoxy, trifluoromethylthio, amino, alkylamino having up to 2 carbon atoms, dialkylamino in each case having up to 2 carbon atoms per alkyl group, acetylamino or benzoylamino, or $R^2$ and $R^3$ form a 5- to 7-membered saturated or unsaturated heterocyclic ring which may contain an oxygen atom, a sulphur atom or an additional nitrogen atom as a heteroatom, which may optionally be substituted by a group $R^{13}$ which represents hydrogen, a straight-chain or branched, saturated or unsaturated alkyl group having up to 10 carbon atoms, which may be optionally substituted by phenyl which may be substituted by halogen, alkyl having up to 4 C atoms, alkoxy having up to 4 C atoms, nitro and haloalkyl having up to 2 C atoms or represent phenyl which may optionally be substituted by halogen, cyano, nitro, alkyl having up to 2 C atoms, alkoxy having up to 2 C atoms or haloalkyl having up to 2 C atoms, $R^4$ and $R^5$ are identical or different and represent hydrogen, fluorine, chlorine, bromine, alkyl having up to 4 carbon atoms, alkoxy having up to 4 carbon atoms, methylthio, cyano, nitro, trifluoromethyl or trifluoromethoxy, represents a group of the formula $-O-(CH_2)n-R^{10}$, $-S-(CH_2)_n-R^{10}$, $-O-SO_2-(CH_2)_n-R^{10}$ or $-O-CO-(CH_2)_n-R^{10}$ in which n denotes 0 to 3, and $R^{10}$ denotes cyclohexyl or phenyl which may be monosubstituted to trisubstituted by identical or different substituents from the series comprising fluorine, chlorine, bromine, cyano, nitro, trifluoromethyl, trifluoromethoxy, alkyl having up to 4 carbon atoms, alkoxy having up to 4 carbon atoms, methylthio, amino, alkylamino having up to 4 carbon atoms, dialkylamino in each case having up to 4 carbon atoms per alkyl group, acetylamino, or denotes pyridyl, thienyl, furyl, pyrimidyl or pyrazinyl, and $R^7$ and $R^8$ are identical or different and in each case represent hydrogen, cycloalkyl having 3 to 7 carbon atoms or represent straight-chain or branched alkyl or alkenyl having up to 14 carbon atoms, which may be substituted by fluorine, chlorine, bromine, hydroxyl, alkoxy having up to 6 carbon atoms, alkylthio having up to 6 carbon atoms, alkylcarbonyl having up to 6 carbon atoms in the alkyl radical, carboxyl, alkoxycarbonyl having up to 6 carbon atoms, or by a phenyl or phenoxy radical optionally substituted by nitro, trifluoromethyl, methyl or methoxy, or where the radicals alkyl and alkenyl are optionally substituted by cyano and/or by a group of the formula —NR$^{11}$R$^{12}$, in which R$^{11}$ and R$^{12}$ are identical or different and in each case denote hydrogen, alkyl having up to 6 carbon atoms, benzyl, phenethyl, phenyl, acetyl, benzoyl, alkylsulphonyl having up to 4 carbon atoms or phenylsulphonyl, or represent phenyl or naphthyl which may be monosubstituted to trisubstituted by identical or different substituents from the series comprising nitro, fluorine, chlorine, bromine, alkyl having up to 4 carbon atoms, alkoxy having up to 4 carbon atoms, alkylthio having up to 4 carbon atoms, trifluoromethyl, trifluoromethoxy, amino, alkylamino having up to 6 carbon atoms, dialkylamino in each case having up to 6 carbon atoms per alkyl group, acetylamino or by benzoylamino, or represent pyrrolidino, pyridino represent piperazino, N—C$_1$-C$_4$-alkylpiperazino, N—C$_7$-C$_9$-aralkyl or N-phenyl-piperazino, and A represents a straight-chain, branched or cyclic, saturated or unsaturated hydrocarbon radical having up to 12 carbon atoms, which may optionally be interrupted by an oxygen or sulphur atom or an N—R$^{14}$ group, in which R$^{14}$ may denote hydrogen, alkyl having up to 2 carbon atoms, benzyl or phenethyl, and/or which may be substituted by halogen, hydroxyl, acetoxy, carboxyl, alkoxycarbonyl having up to 4 carbon atoms or by phenyl which may optionally be substituted by halogen, alkyl having up to 2 carbon atoms, alkoxy having up to 2 carbon atoms, trifluoromethyl or trifluoromethoxy, and their physiologically acceptable salts.

Particularly referred compounds of the general formula (I) are those in which

R$^1$ and R$^9$ are identical or different and represent methyl, ethyl or benzyl, R$^2$ and R$^3$ are identical or different and represent hydrogen, straight-chain or branched alkyl or alkenyl having up to 6 carbon atoms, which may be substituted by hydroxyl, carboxyl, alkoxycarbonyl having up to 4 C atoms in the alkyl radical, or by phenyl which is optionally substituted by nitro, halogen, trifluoromethyl, trifluoromethoxy, methyl or methoxy, or represent cycloalkyl having 3 to 6 carbon atoms or represent phenyl which may be monosubstituted or disubstituted by identical or different substituents from the series comprising nitro, halogen, alkyl having up to 2 carbon atoms, alkoxy having up to 2 carbon atoms, alkylthio having up to 2 carbon atoms, trifluoromethyl, trifluoromethoxy, difluoromethoxy, trifluoromethylthio, amino, alkylamino having up to 2 carbon atoms or dialkylamino in each case having up to 2 carbon atoms per alkyl group, or represent a 5- to 7-membered saturated or unsaturated heterocyclic ring which may contain an oxygen atom, a sulphur atom or an additional nitrogen atom as a heteroatom, which may optionally be substituted by a group R$^{13}$ which denotes hydrogen, alkyl having up to 4 C atoms, benzyl, phenethyl or phenyl optionally substituted by halogen, methyl or methoxy, R$^4$ and R$^5$ may be identical or different and in each case represent hydrogen, fluorine, chlorine, methyl, ethyl, methoxy, ethoxy, nitro or trifluoromethyl, R$^6$ represents a group of the formula —O—(CH$_2$)$_n$R$^{10}$, —S—(CH$_2$)$_n$R$^{10}$, —O—SO$_2$—(CH$_2$)$_n$—R$^{10}$ or —O—CO—(CH$_2$)$_n$—R$^{10}$ in which n denotes 0 to 2 and R$^{10}$ denotes cyclohexyl or phenyl which may be monosubstituted or disubstituted by identical or different substituents from the series comprising fluorine, chlorine, nitro, trifluoromethyl, methyl, methoxy, amino, methylamino, dimethylamino, ethylamino, diethylamino or acetylamino, or denotes an α-, β- or a γ-pyridyl group, R$^7$ represents hydrogen or alkyl having up to 4 carbon atoms and R$^8$ represents hydrogen, cyclopropyl, cyclopentyl or cyclohexyl, or represents straight-chain or branched alkyl or alkenyl having up to 10 carbon atoms, which may be substituted by fluorine, chlorine, hydroxyl, alkoxy having up to 4 carbon atoms, alkylthio having up to 4 carbon atoms, alkylcarbonyl having up to 4 carbon atoms in the alkyl radical, carboxyl, alkoxycarbonyl having up to 4 carbon atoms, phenoxy, phenyl or the abovementioned radicals alkyl and alkenyl are optionally substituted by a group of the formula —NR$^{11}$R$^{12}$, in which R$^{11}$ and R$^{12}$ are identical or different and denote hydrogen, alkyl having up to 4 carbon atoms, benzyl, phenyl or acetyl, or R$^8$ represents phenyl which may be monosubstituted or disubstituted by identical or different substituents from the series comprising nitro, fluorine, chlorine, methyl, methoxy, trifluoromethyl, trifluoromethoxy, amino, alkylamino having up to 2 carbon atoms or dialkylamino in each case having up to 2 carbon atoms per alkyl group and A represents a straight-chain, branched or cyclic, saturated or unsaturated hydrocarbon radical having up to 8 carbon atoms, which is optionally interrupted by an oxygen or sulphur atom or an N—R$^{14}$ group, in which R$^{14}$ may denote hydrogen, alkyl having up to 2 carbon atoms, benzyl or phenethyl, and/or may be substituted by hydroxyl, carboxyl, alkoxycarbonyl having up to 4 carbon atoms or by phenyl which may optionally be substituted by halogen, methyl, methoxy, trifluoromethyl or trifluoromethoxy, and their physiologically acceptable salts.

Very particularly preferred compounds of the general formula (I) are those in which R$^1$ and R$^9$ represent methyl, R$^2$ and R$^3$ identical or different and represent straight-chain or branched alkyl with up to 3 carbon atoms which may be substituted by phenyl which is optionally substituted by methyl or R$^2$ and R$^3$ represent morpholino R$^4$ and R$^5$ represent hydrogen R$^6$ represents a group of the formula —O—(CH$_2$)$_n$—R$^{10}$, —S—(CH$_2$)$_n$—R$^{10}$, —O—SO$_2$—(CH$_2$)$_n$—R$^{10}$ or
—O—CO—(CH$_2$)$_n$—R$^{10}$ in which n denotes 0, 1 or 2 and R$^{10}$ denotes cyclohexyl or phenyl which is optionally substituted by methyl R$^7$ represents hydrogen or alkyl having up to 4 carbon atoms R$^8$ represents hydrogen, cyclopropyl, cyclopentyl or represents straight-chain or branched alkyl with up to 5 carbon atoms which is optionally substituted by hydroxy and A represents the group —CH$_2$—CH$_2$—, and their physiologically acceptable salts.

The compounds of the general formula (I) according to the invention, in which

R$^1$ to R$^9$ and A have the abovementioned meanings, are obtained by a process in which

[A] aldehydes of the general formula (II)

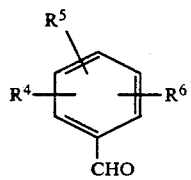
(II)

in which

R$^4$, R$^5$ and R$^6$ have the abovementioned meanings are reacted with β-ketocarboxylic acid esters of the general formula (III)

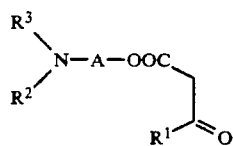
(III)

in which

R$^1$, R$^2$, R$^3$ and A have the abovementioned meanings and if appropriate after isolating the ylidene compounds resulting therefrom of the general formula (IV)

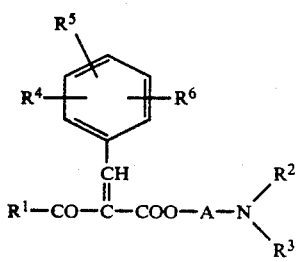
(IV)

in which

R$^1$, R$^2$, R$^3$, R$^4$, R$^5$, R$^6$ and A have the abovementioned meanings, are reacted with β-ketocarboxylic acid amides of the general formula (V)

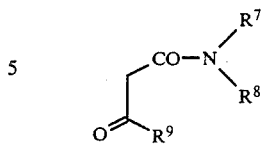
(V)

in which

R$^7$, R$^8$ and R$^9$ have the abovementioned meanings and ammonia or directly with the β-aminocrotonamides prepared therefrom of the general formula (VI)

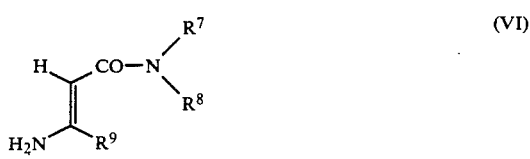
(VI)

in which

R$^7$, R$^8$ and R$^9$ have the abovementioned meanings, or by a process in which

[B] aldehydes of the general formula (II) and β-ketocarboxamides of the general formula (V) or ylidene compounds thereof of the general formula (VII)

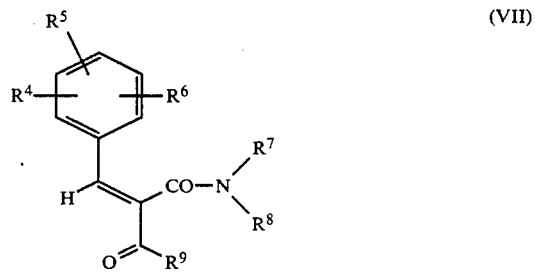
(VII)

in which

R$^4$, R$^5$, R$^6$, R$^7$, R$^8$ and R$^9$ have the abovementioned meanings, are reacted with β-ketocarboxylic acid esters of the general formula (III) and ammonia or directly with the aminocrotonic acid esters prepared therefrom of the general formula (VIII)

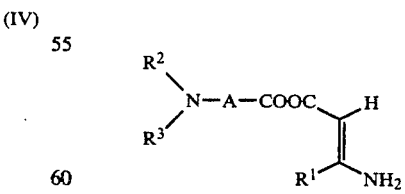
(VIII)

in which

R$^1$, R$^2$, R$^3$ and A have the abovementioned meanings, or by a process in which

[C] dihydropyridinemonocarboxylic acids of the general formula (IXa) or (IXb)

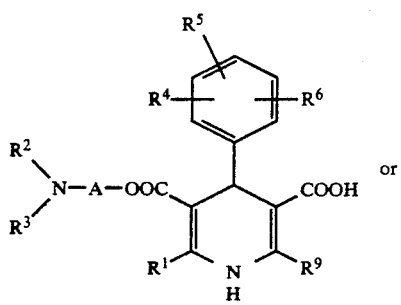
(IXa)

or

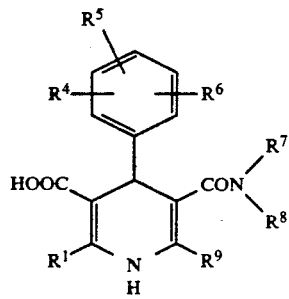
(IXb)

in which
$R^1$, $R^2$, $R^3$, $R^4$, $R^5$, $R^6$, $R^7$, $R^8$, $R^9$ and A have the abovementioned meanings, are reacted, if desired via reactive acid derivatives, with amines of the general formula (Xa)

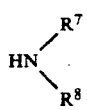
(Xa)

in which
$R^7$ and $R^8$ have the abovementioned meanings, or with compounds of the formula (Xb)

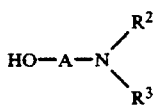
(Xb)

in which
$R^2$, $R^3$ and A have the abovementioned meanings, where, of course, in each case only (IXa) is reacted with (Xa) and (IXb) with (Xb).

Enantiomerically pure compounds of the formula (I) are obtained, for example, by a process in which diastereomer mixtures of the formulae (XIa*) or (XIb*)

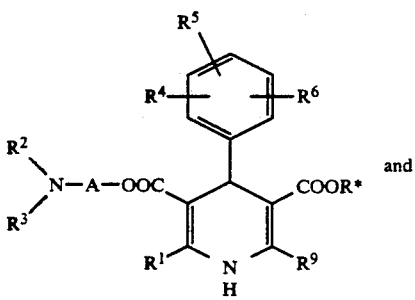
(XIa*)

and

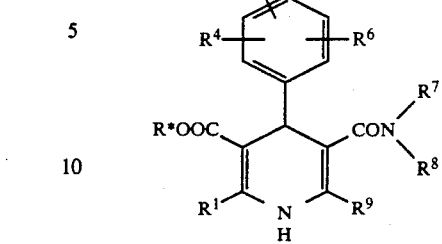
(IXb*)

in which $R^1$, $R^2$, $R^3$, $R^4$, $R^5$, $R^6$, $R^7$, $R^8$, $R^9$ and A have the above-mentioned meanings and
R* represents an optically active ester radical, are separated into the individual diastereomers by crystallization, chromatography or Craig partition, if desired, the optically active ester radical is split off and the enantiomerically pure carboxylic acids of the formulae (IXa*) and (IXb*)

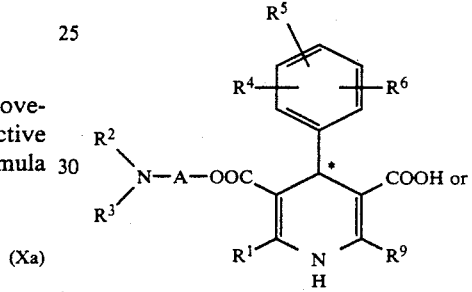
(IXa*)

or

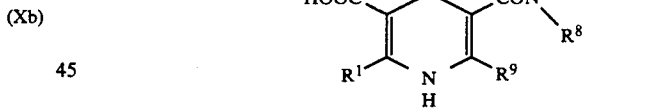
(IXb*)

are then prepared, and the compounds of the general formula (IXa*) are reacted with compounds of the general formula (Xa)

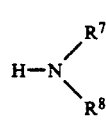
(Xa)

in which
$R^7$ and $R^8$ have the abovementioned meanings, if appropriate via activated acid derivatives or by a process in which compounds of the general formula (IXb*) are reacted with compounds of the general formula (Xb)

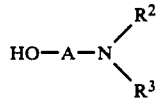
(Xb)

in which
R² R³ and A have the abovementioned meanings, if appropriate via activated acid derivatives.

Depending on the type of starting substances used, the synthesis variants for the compounds according to the invention may be illustrated by the following equations.

Examples of reactive acid derivatives which may be mentioned are: activated esters, hydroxysuccinimide esters, acid imidazolides, acid halides, mixed anhydrides or reaction in the presence of cyclohexylcarbodiimide.

Variant A

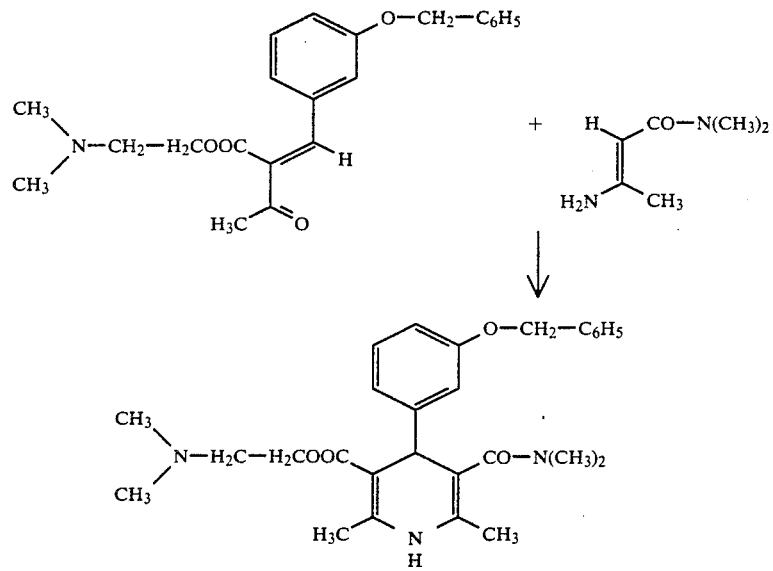

Variant B

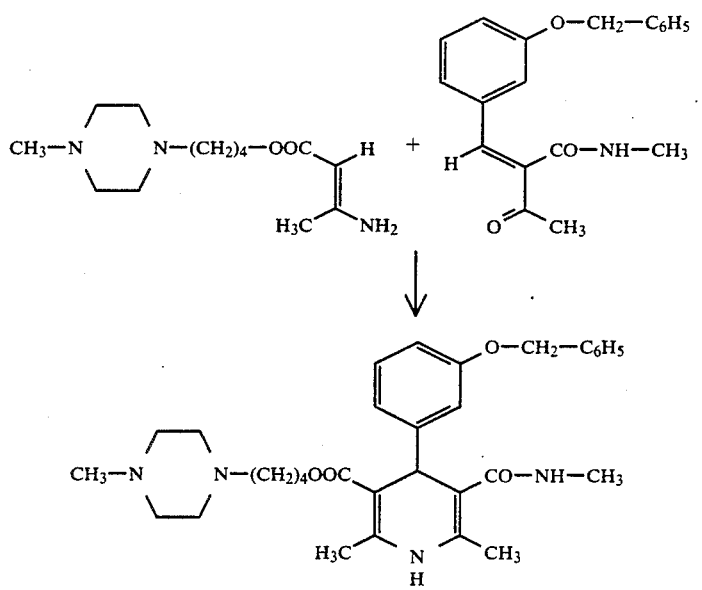

Variant C

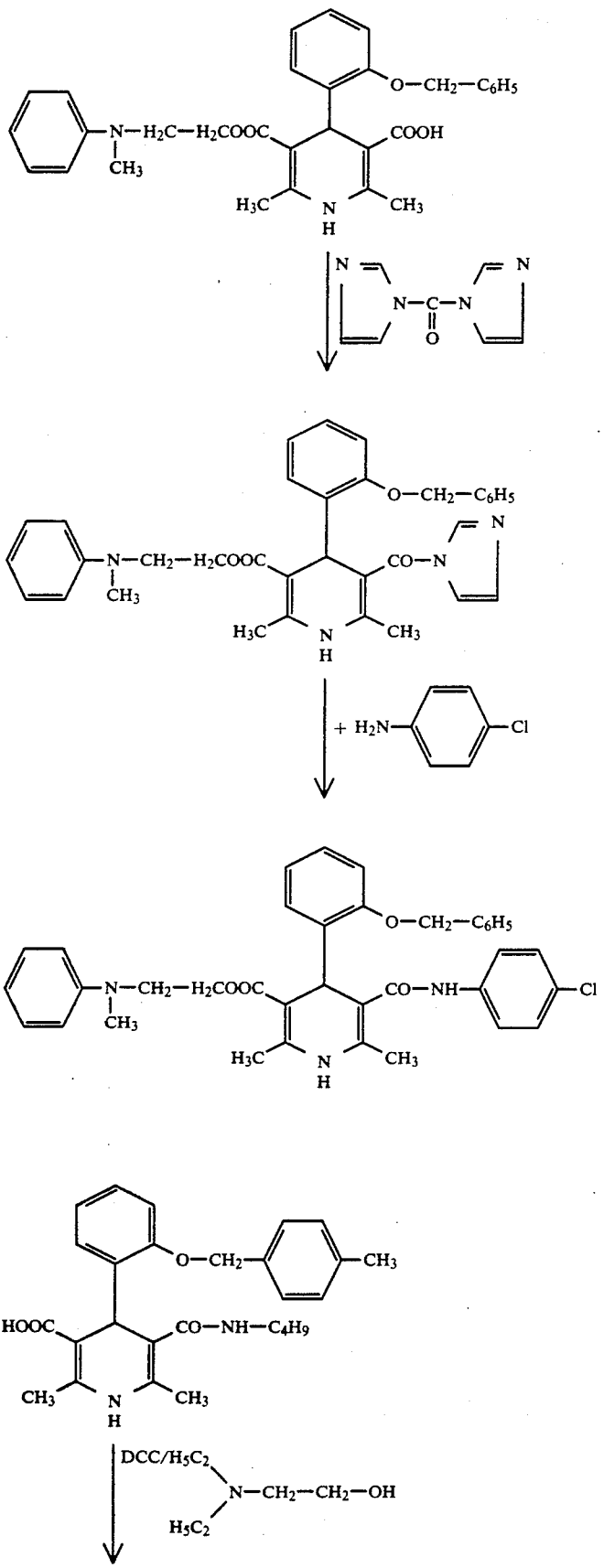

-continued

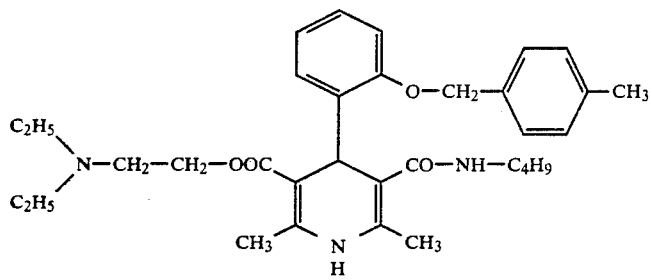

For process A and B, the proviso applies that if $R^2$ and/or $R^3$ denote hydrogen, the amino group is first blocked with an amino protective group, such as, for example, tert.-butyloxycarbonyl or phthalimide and the compounds of the general formula (I)

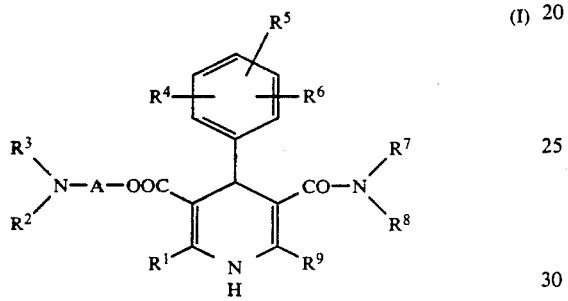

(I)

in which
$R^1$, $R^4$, $R^5$, $R^6$, $R^7$, $R^8$, $R^9$ and A have the abovementioned meanings and $R^2$ and/or $R^3$ denote hydrogen, are then prepared by splitting off the amino protective group by known methods.

Process variants A–C

Possible solvents are water or all inert organic solvents which do not change under the reaction conditions. These preferably include alcohols such as methanol, ethanol, propanol, isopropanol, ethers such as diethyl ether, dioxane, tetrahydrofuran, glycol monomethyl ether or glycol dimethyl ether, or amides such as dimethylformamide, dimethylacetamide or hexamethylphosphoramide, or glacial acetic acid, dimethyl sulphoxide, acetonitrile or pyridine.

The reaction temperatures can be varied within a relatively wide range. In general, the reaction is carried out between $+10°$ C. and $+150°$ C., preferably between $20°$ C. and $+100°$ C., in particular at the boiling point of the respective solvent.

The reaction can be carried out at atmospheric pressure, but also at elevated or reduced pressure. In general, the reaction is carried out at atmospheric pressure.

When carrying out process variants A–C according to the invention, the ratio of the substances participating in the reaction is arbitrary. In general however, molar amounts of reactants are used. The substances according to the invention are isolated and purified in such a way that the solvent is removed by distillation in vacuo and the residue, optionally first obtained crystalline by ice cooling, is recrystallized from a suitable solvent. In some cases it may be necessary to purify the compounds according to the invention by chromatography.

The aldehydes of the general formula (II) employed as starting substances are known or can be prepared by known methods [DOS 2,165,260; 2,401,665; T. D. Harris, G. P. Roth, J. Org. Chem. 44, 2004 (1979); W. J. Dale, H. E. Hennis, J. Am. Chem. Soc. 78, 2543 (1956); Chem. Abstr. 59 13929 (1963)].

The $\beta$-ketocarboxylic acid esters of the general formula (III) employed as starting substances are known or can be prepared by known methods [D. Borrmann in Houben Weyl's "Methoden der organischen Chemie" (Methods of Organic Chemistry) Vol. VII/4, 230 (1968); Y. Oikawa, K. Sugano, O. Yonemitsu, J. Org. Chem. 43, 2087 (1978)] [DOS 1,142,859].

The enamines of the general formulae (VI) and (VIII) employed as starting substances are known or can be prepared by known methods [DOS 2,228,377] [F. A. Glickman, A. C. Cope, J. Am. Chem. Soc. 67, 1017 (1945)].

The ylidene-$\beta$-ketocarboxylic acid derivatives of the general formulae (IV) and in (VII) employed as starting substances are known or can be prepared by known methods [G. Jones "The Knoevenagel Condensation" in Organic Reactions vol. XV, 204 (1967)].

Process variant C according to the invention is carried out following the method known from the literature for the conversion of carboxylic acids into carboxylic acid amides. In this method, the carboxylic acid is first converted into an activated form, such as, for example, the acid chloride or the imidazolide, which is either isolated as such and reacted in a second reaction step, or which is amidated directly in situ to give the compounds according to the invention. Examples of activating reagents which may be mentioned in addition to the inorganic halides such as thionyl chloride, phosphorus trichloride or phosphorus pentachloride, or carbonyldiimidazole, are carbodiimides such as cyclohexylcarbodiimide or 1-cyclohexyl-3-[2-(N-methylmorpholino)-ethyl]carbodiimide p-toluenesulphonate or N-hydroxyphthalimide or N-hydroxy-benzotriazole in the presence of dicyclohexylcarbodiimide. Naturally, the dihydropyridinemonocarboxylic acids may also be employed in the form of their salts. [The method of amidation is described, for example, in: Fieser & Fieser, Reagents for Organic Synthesis, John Wiley & Sons Inc. (1967), pages 231–236; J. C. Shihan and G. P. Hess, J. Am. Chem. Soc. 77, 1067 (1955); U. Goodman, G. W. Kenner, Adv. in Protein Chem. 12, 488 (1957); W. A. Bonner, P. I. McNamee, J. Org. Chem. 26, 254 (1961); H. A. Staab, Angew. Chemie Int. Ed. 1, 351 (1962); Fieser & Fieser, Reagents for Organic Synthesis, John Wiley & Sons Inc. 1967, 116, 114; H. C. Beyerman, U. O. van der Brink, Re. Trav. 80, 1372 (1961); C. A. Buehler, D. E. Pearson, John Wiley & Sons, Volume 1 (1970), page 895 ff, Volume II, (1977)].

In addition to water, suitable solvents for process variant C are all inert organic solvents which do not change under the reaction conditions. These preferably include ethers such as diethyl ether, dioxane, tetrahydrofuran, glycol monomethyl ether or glycol dimethyl ether, or halogenated hydrocarbons such as dichloromethane, trichloromethane or tetrachloromethane, or amides such as dimethylformamide, dimethylacetamide or hexamethylphosphoramide, or hydrocarbons such as benzene, toluene or xylene, or acetonitrile, nitromethane, pyridine, dimethyl sulphoxide or ethyl acetate. Mixtures of the solvents mentioned may also be used. If the activated intermediates of the dihydropyridinemonocarboxylic acids are isolated, the amines of the formula (Xa) may also be used alone as diluents.

The reaction temperatures may be varied within a wide range. In general, the reaction is carried out in a range from $-70°$ C. to $+140°$ C., preferably from $-20°$ C. to $+100°$ C.

The reaction may be carried out at atmospheric pressure, but also at elevated or reduced pressure. In general, the reaction is carried out at atmospheric pressure.

When carrying out process variant C according to the invention, the ratio of the substances participating in the reaction is arbitrary. In general, however, molar amounts of reactants are used. However, it has proved favorable to employ the amine in a 5- to 10-fold molar excess. It is particularly expedient to employ the amine in a large excess directly as the solvent.

The dihydropyridinemonocarboxylic acids of the general formulae (IXa) and (IXb) employed as starting substances are not known but can be prepared by known methods [DOS 2,847,236; 3,206,671; 2,962,241].

The amines of the general formulae (Xa) and (Xb) employed as starting substances are known or can be prepared by known methods [Houben Weyl's "Methoden der organischen Chemie" ("Methods of Organic Chemistry") Vol. XI/1; Paulsen, Angewandte Chemie 78, 501-566 (1966)].

The amino protective group is removed in a manner known per se under acidic conditions, or if it represents the phthalimide radical, the protective group is customarily removed using hydrazine hydrate in organic solvents such as ethers, for example tetrahydrofuran or dioxane, or alcohols, for example methanol, ethanol or isopropanol.

The compounds according to the invention show an unforeseeable, useful spectrum of pharmacological action. They influence the contractility of the heart, the tone of the smooth musculature and the electrolyte and fluid balance.

They can therefore be employed in medicaments for the treatment of pathologically changed blood pressure and cardiac insufficiency, and also as coronary therapeutics. Moreover, they can be employed for the treatment of cardiac arrhythmias, renal insufficiency, cirrhosis of the liver, ascites, pulmonary oedema, cerebral oedema, oedema of pregnancy, glaucoma or diabetes mellitus.

The cardiac action of the compounds according to the invention was established on isolated, stimulated guinea-pig heart papillary muscle. For this purpose, the experimental animals (200 g guinea-pigs of both sexes) were sacrificed, the thorax was opened and the heart was removed. For the experiments, in each case the smallest possible papillary muscles were then dissected out of the right ventricle, and fixed horizontally in an organ bath. One end of the muscle was held by two metal electrodes which were at the same time used to stimulate the preparation, while the other end of the muscle was connected to a force transducer via a thread. The papillary muscle was stimulated supraliminally using a frequency of 1 Hz. A Krebs-Henseleit solution (concentration in mM): NaCl 118; NaHCO$_3$ 25; KCl 10; KH$_2$PO$_4$ 1.2; MgSO$_4$ 1.2; CaCl$_2$ 1.8; glucose 10, pH 7.4) was continuously passed through the organ bath having a volume of about 2 ml at a rate of 4 ml/min and a temperature of 32° C. The contractions of the papillary muscle were measured isometrically by means of the attached force transducer and recorded on a recorder.

The substances according to the invention were dissolved in the Krebs-Henseleit solution in a concentration of 10 $\mu$g/ml, if desired using a solubilizer (DMSO up to a concentration of 0.5%). The dihydropyridinecarboxamides according to the invention in this case showed an inhibition of the contractility of the papillary muscle by more than 10% relative to the control value.

In order to test the renal effect, the substances were administered orally to conscious male Wistar rats. After loading with physiological saline solution, the sodium excretion was measured in metabolic cages.

The new active compounds may be converted in a known manner into the customary formulations, such as tablets, coated tablets, pills, granules, aerosols, syrups, emulsions, suspensions and solutions, using inert, non-toxic, pharmaceutically suitable excipients or solvents. In this case, the therapeutically active compound should in each case be present in a concentration of about 0.5 to 90% by weight of the total mixture, i.e. in amounts which are sufficient to achieve the dosage range indicated.

The formulations are prepared, for example, by extending the active compound with solvents and/or excipients, optionally using emulsifiers and/or dispersants, where, for example, in the case of the use of water as a diluent, organic solvents may optionally be used as auxiliary solvents.

Examples of auxiliaries which may be mentioned are: water, non-toxic organic solvents, such as paraffins (for example mineral oil fractions), vegetable oils (for example groundnut/sesame oil), alcohols (for example: ethyl alcohol, glycerol), excipients, for example ground natural minerals (for example kaolins, aluminas, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkylsulphonates, arylsulphonates), detergents (for example lignin-sulphite waste liquors, methylcellulose, starch and polyvinylpyrrolidone) and lubricants (for example magnesium stearate, talc, stearic acid and sodium lauryl sulphate.

Administration is carried out in a customary manner, preferably orally or parenterally, in particular perlingually or intravenously. In the case of oral administration, tablets may, of course, also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc may additionally be used for tableting. In the case of aqueous suspensions, various flavor enhancers or colorants may be added to the active compounds in addition to the abovementioned auxiliaries.

In the case of parenteral administration, solutions of the active compound using suitable liquid carrier materials may be employed.

In general, it has proved advantageous on intravenous administration to administer amounts of about 0.001 to 1 mg/kg, preferably about 0.01 to 0.5 mg/kg of body weight to attain effective results, and on oral administration the dosage is about 0.01 to 20 mg/kg, preferably 0.1 to 10 mg/kg of body weight.

In spite of this, it may sometimes be necessary to deviate from the amounts mentioned, depending on the body weight or the type of administration route, on individual behavior towards the medicament, the manner of its formulation and the point in time or interval at which administration takes place. Thus, in some cases it may be sufficient to manage with less than the minimum amount previously mentioned, whereas in other cases the upper limit mentioned must be exceeded. In the case of the administration of larger amounts, it may be advisable to divide these into a number of individual doses over the day.

PREPARATION EXAMPLES

Example 1

Process variant B

N-Cyclopropyl 1,4-dihydro-2,6-dimethyl-3-[2-(N-morpholinoethoxycarbonyl)]-4-(2-benzyloxyphenyl)-pyridine-5-carboxamide hydrochloride

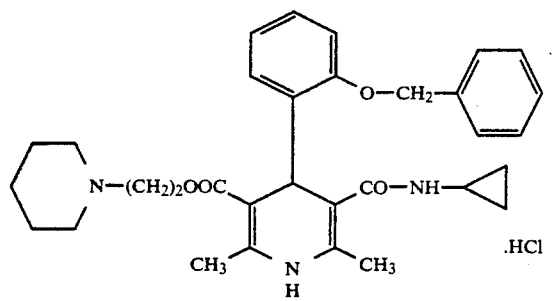

3.4 g (10 mmol) of N-cyclopropyl 2-benzyloxybenzylidene-acetoacetamide are boiled under argon for 18 hours in 30 ml of isopropanol with 2.1 g (10 mmol) of 2-(N-morpholino)-ethyl β-aminocrotonate and concentrated. The oily residue obtained is purified by means of a silica gel column using toluene/acetone as the eluent, and the clean fractions are combined and concentrated. The oily evaporation residue is dissolved in ether, HCl/ether is added, the mixture is concentrated, ethanol is added to the residue twice and the mixture is concentrated twice, and the residue is stirred with acetonitrile, filtered off with suction and washed with acetonitrile. 1 g of a colorless substance of melting point 130° C. with decomposition is obtained.

Example 2

Process variant C

N-Ethyl 1,4-dihydro-2,6-dimethyl-3-(2-dimethylamino-ethoxycarbonyl)-4-(2-(4-methylbenzyloxy)-phenyl)-pyridine-5-carboxamide hydrochloride

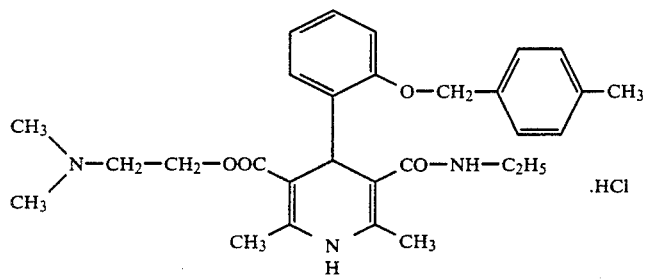

2 g (3.9 mmol) of 1,4-dihydro-2,6-dimethyl-3-(2-dimethylaminoethoxycarbonyl)-4-[2-(4-methylbenzyloxy)-phenyl]-5-carboxylic acid imidazolide are stirred in 20 ml of 50% strength ethylamine solution for 20 hours. The mixture is concentrated, the residue is taken up in ethyl acetate, and the solution is washed twice with water, dried and concentrated. The oily substance is purified by silica gel chromatography using toluene/ethanol. The clean fractions are concentrated and converted into the hydrochloride. 1.1 g of colorless crystals of melting point 147° C. with decomposition are obtained.

Example 3

Process variant A

N-Propyl 1,4-dihydro-2,6-dimethyl-3-(2-N-benzyl-N-methylaminoethoxycarbonyl)-4-(2-benzyloxyphenyl)-pyridine-5-carboxamide

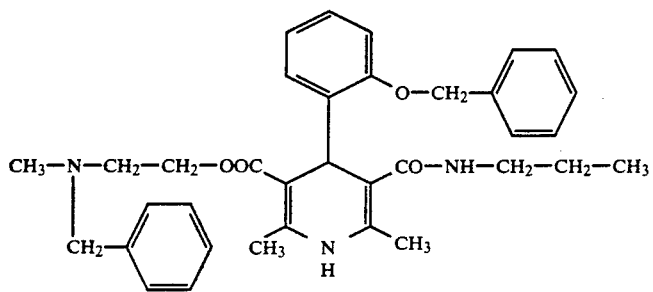

10 g (22.5 mmol) of 2-N-benzyl-N-methylaminoethyl-2-benzyloxy-benzylidene-acetoacetate are boiled under argon with 3.2 g (22.5 mmol) of N-propyl β-amino crotonamide in 50 ml of isopropanol for 4 hours. The mixture is concentrated, the residue is taken up in ethyl acetate, and the solution is washed twice with water, dried and concentrated. The evaporation residue is purified by means of a silica gel column using toluene/ethyl acetate 1:1. The pure fractions are crystallized by stirring with ether. 5.5 g of crystals of melting point 100° C. are obtained.

| Example No. | Formula | Melting Points (R$_F$ value*) | Process |
|---|---|---|---|
| 4 |  | (1) 0.46 | C |
| 5 |  | (1) 0.51 | C |
| 6 |  | (1) 0.5 | C |

-continued

| Example No. | Formula | Melting Points (R_F value*) | Process |
|---|---|---|---|
| 7 | 4-(2-((4-methylbenzyl)oxy)phenyl)-3-(N-methylcarbamoyl)-5-((2-(N-benzyl-N-methylamino)ethoxy)carbonyl)-2,6-dimethyl-1,4-dihydropyridine | (1) 0.5 | C |
| 8 | 4-(2-((4-methylbenzyl)oxy)phenyl)-3-(N-ethylcarbamoyl)-5-((2-(N-benzyl-N-methylamino)ethoxy)carbonyl)-2,6-dimethyl-1,4-dihydropyridine | (1) 0.53 | C |
| 9 | 4-(2-((4-methylbenzyl)oxy)phenyl)-3-(N-cyclopropylcarbamoyl)-5-((2-(N-benzyl-N-methylamino)ethoxy)carbonyl)-2,6-dimethyl-1,4-dihydropyridine | (1) 0.52 | C |
| 10 | 4-(2-((4-methylbenzyl)oxy)phenyl)-3-(N-(5-hydroxypentyl)carbamoyl)-5-((2-(N-benzyl-N-methylamino)ethoxy)carbonyl)-2,6-dimethyl-1,4-dihydropyridine | (1) 0.26 | C |
| 11 | 4-(2-((4-methylbenzyl)oxy)phenyl)-3-(N-methylcarbamoyl)-5-((2-(N,N-dimethylamino)ethoxy)carbonyl)-2,6-dimethyl-1,4-dihydropyridine | 90–95° C. | C |

-continued

| Example No. | Formula | Melting Points (R_F value*) | Process |
|---|---|---|---|
| 12 | (structure) | 159° C. | A |
| 13 | (structure) | 143° C. | A |
| 14 | (structure) | 120° C. | A |
| 15 | (structure) | 155° C. (decomp.) | B |
| 16 | (structure) | 145–148° C. (decomp.) | A |

-continued
| Example No. | Formula | Melting Points (R_F value*) | Process |
|---|---|---|---|
| 17 | 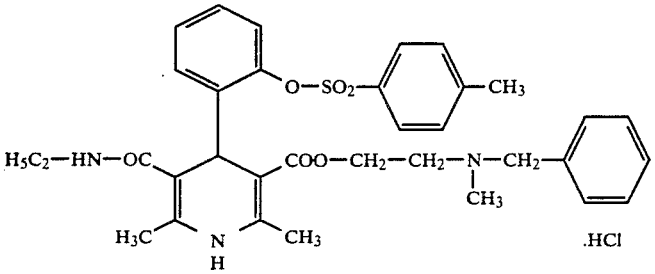 | 225° C. (decomp.) | A |
| 18 | 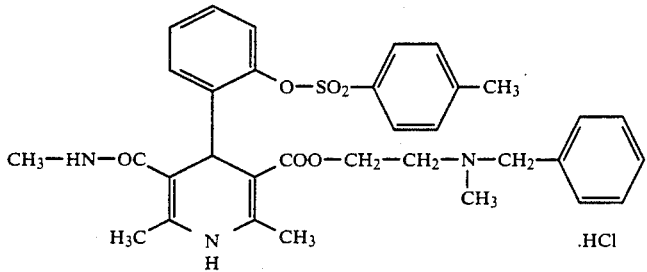 | 177–180° C. | A |
| 19 | 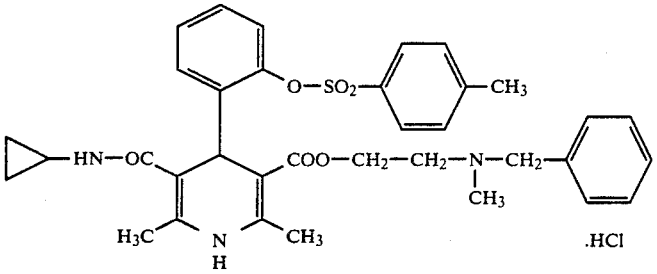 | 237–239° C. (decomp.) | A |
| 20 | 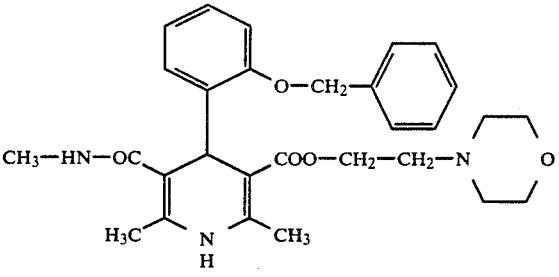 | (1) 0.25 | A |
| 21 | 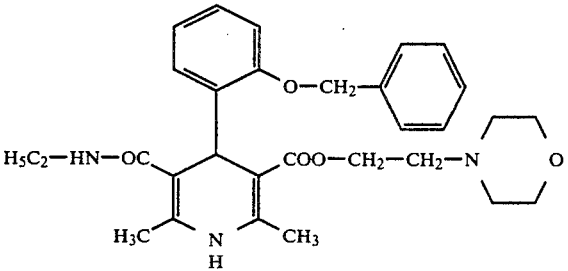 | (1) 0.31 | A |

| Example No. | Formula | Melting Points (R_F value*) | Process |
|---|---|---|---|
| 22 | 2-benzyloxyphenyl dihydropyridine with CH₃—CH₂—CH₂—HN—OC and COO—CH₂—CH₂—N(morpholino); 2,6-dimethyl-1,4-dihydropyridine | (1) 0.35 | A |
| 23 | 2-benzyloxyphenyl dihydropyridine with cyclopropyl-HN—OC and COO—CH₂—CH₂—N(morpholino); 2,6-dimethyl-1,4-dihydropyridine | (1) 0.29 | A |
| 24 | 2-(benzylthio)phenyl dihydropyridine with CH₃—HN—OC and COO—CH₂—CH₂—N(CH₃)(CH₂-phenyl); 2,6-dimethyl-1,4-dihydropyridine | (1) 0.41 | A |
| 25 | 2-(benzylthio)phenyl dihydropyridine with CH₃—(CH₂)₂—HN—OC and COO—CH₂—CH₂—N(CH₃)(CH₂-phenyl); 2,6-dimethyl-1,4-dihydropyridine | (1) 0.48 | A |
| 26 | 2-(benzylthio)phenyl dihydropyridine with cyclopropyl-HN—OC and COO—CH₂—CH₂—N(CH₃)(CH₂-phenyl); 2,6-dimethyl-1,4-dihydropyridine | 84–86° C. | A |

-continued

| Example No. | Formula | Melting Points (R_F value*) | Process |
|---|---|---|---|
| 27 | | (1) 0.42 | A |
| 28 | | (2) 0.77 | A |
| 29 | | (2) 0.74 | A |
| 30 | | (2) 0.72 | A |
| 31 | | 194–197° C. (2) 0.63 | A |

*R_F values eluent:
(1) toluene/acetone (1:1) Merck prepared TLC Plates, Silica gel 60 F 254
(2) methylenechloride/methanol (10:1) HPTLC prepared plates, Silica gel 60 F 254

Example 32

N-Ethyl 3-(2-aminoethoxycarbonyl)-4-(2-benzyloxyphenyl)-1,4-dihydro-2,6-dimethyl-pyridine-5-carboxamide

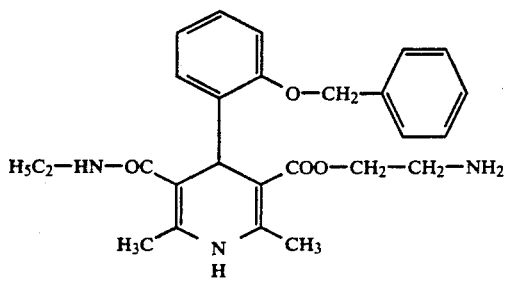

A solution of 11.0 g (18.97 mmol) of N-ethyl 4-(2-benzyloxyphenyl)-1,4-dihydro-2,6-dimethyl-3-(2-phthalimido-ethoxycarbonyl)-pyridine-5-carboxamide (Example 28) and 95.0 mmol of hydrazine hydrate are heated under reflux in 100 ml of ethanol for 2 h. The solution is then cooled and the residue is filtered. The latter is subsequently washed with methylene chloride and the filtrate is concentrated in vacuo. The concentrated residue is then washed once with a 2 N solution of potassium hydroxide and then 3 times with water. The product is purified on a silica gel column using methylene chloride/methanol mixtures.

Yield: 6.56 g (76.9% of theory)

The product is amorphous.

The examples listed in the following table were prepared analogously to the directions for Example 32.

| Example No. | Formula | Melting Point ($R_F$ value*) |
|---|---|---|
| 33 | 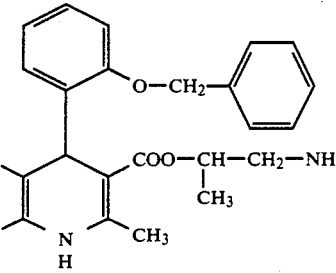 | (3) 0.66 |
| 34 | 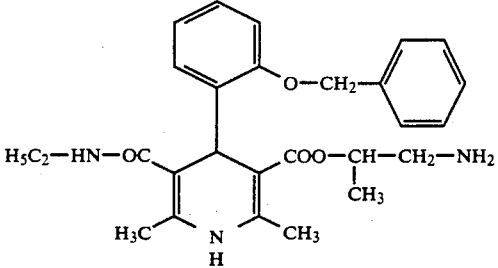 | (3) 0.61 |
| 35 | 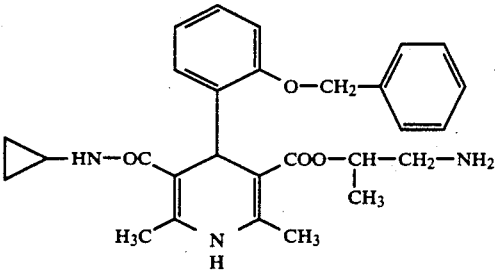 | (3) 0.67 |
| 36 | 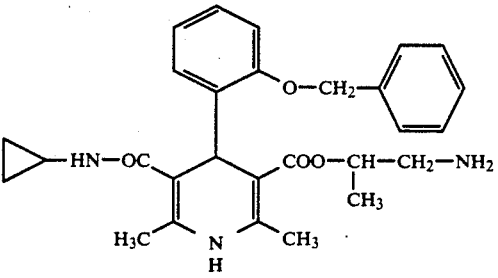 | (3) 0.64 |

-continued

| Example No. | Formula | Melting Point (R_F value*) |
|---|---|---|
| 37 | 2-benzyloxyphenyl-dihydropyridine with cyclopropyl-NHCO- and -COO-CH₂-CH₂-NH₂ substituents, 2,6-dimethyl | 179–181° C. |
| 38 | 2-(cyclohexylmethoxy)phenyl-dihydropyridine with CH₃-NHCO- and -COO-CH₂-CH₂-N(CH₃)(CH₂C₆H₅), 2,6-dimethyl | 140–144° C. |
| 39 | 2-(cyclohexylmethoxy)phenyl-dihydropyridine with C₂H₅-NHCO- and -COO-CH₂-CH₂-N(CH₃)(CH₂C₆H₅), 2,6-dimethyl | (4) 0.54 |
| 40 | 2-(cyclohexylmethoxy)phenyl-dihydropyridine with cyclopropyl-NHCO- and -COO-CH₂-CH₂-N(CH₃)(CH₂C₆H₅), 2,6-dimethyl | (4) 0.54 |
| 41 | 2-(benzoyloxy)phenyl-dihydropyridine with CH₃-NHCO- and -COO-CH₂-CH₂-N(CH₃)(CH₂C₆H₅), 2,6-dimethyl | (4) 0.35 |

-continued

| Example No. | Formula | Melting Point (R$_F$ value*) |
|---|---|---|
| 42 | [structure: 4-(2-benzyloxyphenyl)-dihydropyridine with C$_2$H$_5$—NH—OC and COO—CH$_2$—CH$_2$—N(CH$_3$)(CH$_2$C$_6$H$_5$) substituents; 2,6-dimethyl; −Enantiomer] | 112° C. |
| 43 | [structure: 4-(2-benzoyloxyphenyl)-dihydropyridine with C$_2$H$_5$—NH—OC and COO—CH$_2$—CH$_2$—N(CH$_3$)(CH$_2$C$_6$H$_5$) substituents; 2,6-dimethyl] | (4) 0.40 |
| 44 | [structure: 4-(2-benzyloxyphenyl)-dihydropyridine with C$_2$H$_5$—NH—OC and COO—CH$_2$—CH$_2$—N(CH$_3$)(CH$_2$C$_6$H$_5$) substituents; 2,6-dimethyl; +Enantiomer] | 110° C. |
| 45 | [structure: 4-(2-benzoyloxyphenyl)-dihydropyridine with C$_3$H$_7$—HN—OC and COO—CH$_2$—CH$_2$—N(CH$_3$)(CH$_2$C$_6$H$_5$) substituents; 2,6-dimethyl] | (4) 0.42 |

*R$_F$ values eluent:
(3) methylene chloride/methanol (5:1)
(4) toluene/acetone 1:1

It will be appreciated that the instant specification and claims are set forth by way of illustration and not limitation, and that various modifications and changes may be made without departing from the spirit and scope of the present invention.

What is claimed is:

1. A dihydropyridine amide of the formula

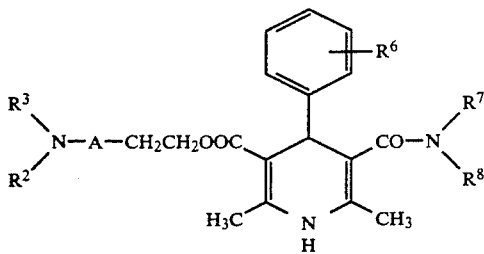

in which
R² and R³ carbon atoms, one of which is substituted by, and the other of which is optionally substituted by, halogen, alkoxy having up to 8 carbon atoms, trifluoromethyl or phenyl which is optionally substituted by methyl, R⁶ represents a group of the formula —O—(CH₂)$_n$—R¹⁰, —S—(CH₂)$_n$—R¹⁰,
—O—SO₂—(CH₂)$_n$—R¹⁰ or
—O—CO—(CH₂)$_n$—R¹⁰ in which
R¹⁰ denotes cyclohexyl or phenyl which is optionally substituted by methyl, R⁷ represents hydrogen or alkyl having up to 4 carbon atoms, and R⁸ represents hydrogen, cyclopropyl, cyclopentyl or represents straight-chain or branched alkyl with up to 5 carbon atoms which is optionally substituted by hydroxy, or a physiologically acceptable salt thereof.

2. A compound according to claim 1, wherein such compound is N-propyl 1,4-dihydro-2,6-dimethyl-3-(2-N-benzyl-N-methylaminoethoxycarbonyl)-4-(2-benzyloxyphenyl)-pyridine-5-carboxamide of the formula

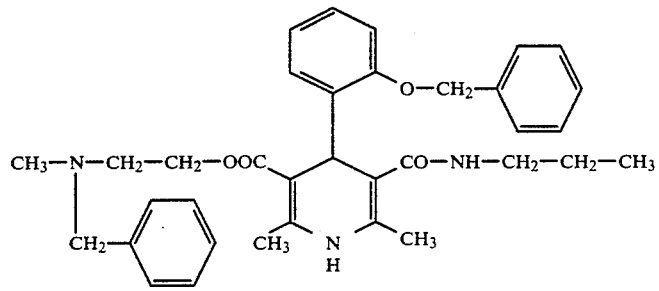

or a physiologically acceptable salt thereof.

3. A compound according to claim 1, wherein such compound is N-ethyl 1,4-dihydro-2,6-dimethyl-3-(2-N-benzyl-N-methylaminoethoxycarbonyl)-3-(2-benzyloxyphenyl)-pyridine-5-carboxamide of the formula

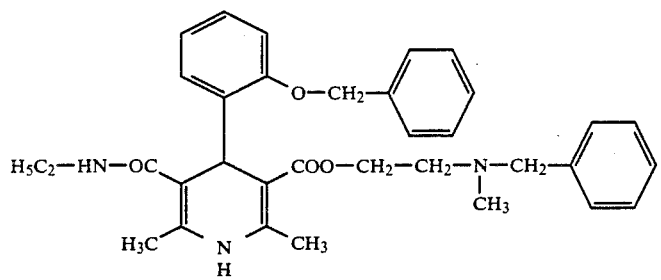

or a physiologically acceptable salt thereof.

4. A compound according to claim 1, wherein such compound is N-ethyl 1,4-dihydro-2,6-dimethyl-3-(2-N-benzyl-N-methylaminoethoxycarbonyl)-4-[2-(4-tolyl-sulphonyloxyphenyl)]-pyridine-5-carboxamide of the formula

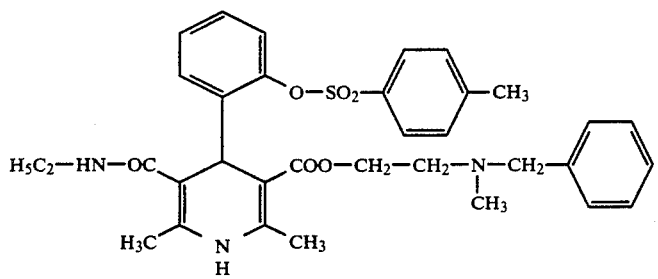

or a physiologically acceptable salt thereof.

5. A compound according to claim 1, wherein such compound is N-ethyl 1,4-dihydro-2,6-dimethyl-3-(2-benzyl-N-methylaminoethoxycarbonyl)-4-(2-cyclohexylmethoxy)-pyridine-5-carboxamide of the formula

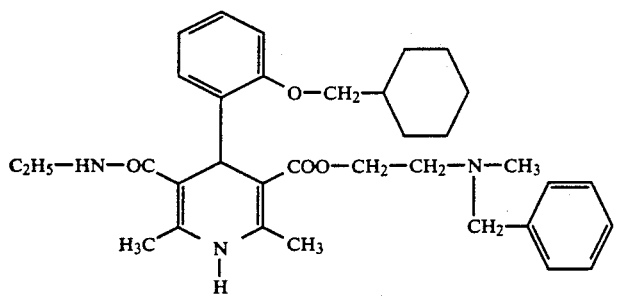

or a physiologically acceptable salt thereof.

6. A compound according to claim 1, wherein such compound is N-methyl 1,4-dihydro-2,6-dimethyl-3-(2-N-benzyl-N-methylaminoethoxycarbonyl)-4-(2-benzyloxyphenyl)-pyridine-5-carboxamide of the formula

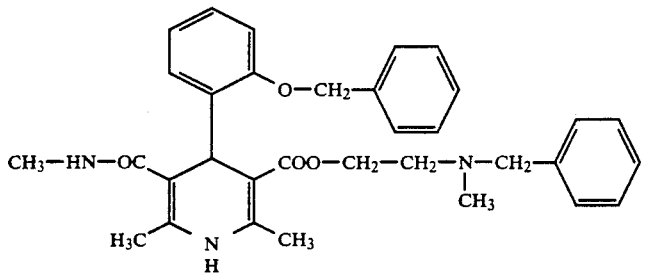

or a physiologically acceptable salt thereof.

7. A compound according to claim 1, wherein such compound is N-cyclopropyl 1,4-dihydro-2,6-dimethyl-3-(2-N-benzyl-N-methyl-aminoethoxycarbonyl)-4-(2-benzyloxyphenyl)-pyridine-5-carboxamide of the formula

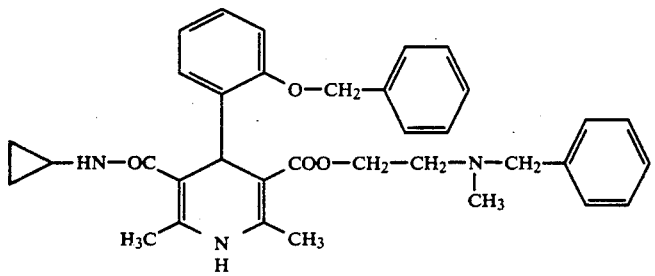

or a physiologically acceptable salt thereof.

8. A compound according to claim 1, wherein such compound is N-methyl 1,4-dihydro-2,6-dimethyl-3-(2-benzyl-N-methyl-aminoethoxycarbonyl)-4-(2-benzythiophenyl)-pyridine-5-carboxamide of the formula

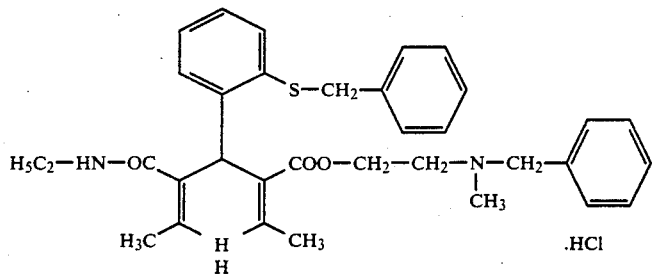

or a physiologically acceptable salt thereof.

9. An anti-arrhythmic composition comprising an amount effective therefor of a compound or salt according to claim 1 and a pharmaceutically acceptable diluent.

10. A composition for treating renal insufficiency comprising an amount effective therefor of a compound or salt according to claim 1 and a pharmaceutically acceptable diluent.

* * * * *